United States Patent
Raber et al.

(10) Patent No.: US 8,465,932 B2
(45) Date of Patent: Jun. 18, 2013

(54) **METHOD FOR THE DETERMINATION OF *TRICHINELLA* INFECTIONS AND DIAGNOSTIC COMPOSITION FOR SUCH METHODS**

(75) Inventors: Alex Raber, Zurich (CH); Tina Haupt, Rudlingen (CH); Patrik Buholzer, Winterthur (CH)

(73) Assignee: Prionics AG, Schlieren (CH)

( * ) Notice: Subject to any disclaimer, the term of this patent is extended or adjusted under 35 U.S.C. 154(b) by 132 days.

(21) Appl. No.: 12/937,129

(22) PCT Filed: Jun. 16, 2009

(86) PCT No.: PCT/EP2009/004309
§ 371 (c)(1),
(2), (4) Date: Oct. 8, 2010

(87) PCT Pub. No.: WO2009/156075
PCT Pub. Date: Dec. 30, 2009

(65) Prior Publication Data
US 2011/0033871 A1    Feb. 10, 2011

(30) Foreign Application Priority Data
Jun. 27, 2008  (DE) .......................... 10 2008 030 129

(51) Int. Cl.
*G01N 33/53* (2006.01)
(52) U.S. Cl.
USPC ........................................... 435/7.1; 436/518
(58) Field of Classification Search
None
See application file for complete search history.

(56) References Cited

U.S. PATENT DOCUMENTS

2010/0098717 A1    4/2010   Boireau et al.
2010/0190182 A1    7/2010   Buholzer et al.

FOREIGN PATENT DOCUMENTS

| EP | 0324849 B1 | 10/1995 |
| WO | 2007/090960 A1 | 8/2007 |
| WO | 2009/003497 A1 | 1/2009 |

OTHER PUBLICATIONS

Reiterova et al. (Infection 2007, vol. 35, p. 89-93).*
Bien et al. (Wiad Parazytol 2007 vol. 53, p. 149-151; English Abstract only).*
International Preliminary Report on Patentability for International Application No. PCT/EP2009/004309 dated Feb. 10, 2011.
Bien, Justyna; "The usefulness of ELISA test for early serological detection of *Trichinella* spp. infection in pigs"; The Doctoral Thesis conducted in the Parasitology Institute PAN (Polish Academy of Sciences), Warsaw, Poland, defended on Oct. 24, 2006.

* cited by examiner

*Primary Examiner* — Jacob Cheu
(74) *Attorney, Agent, or Firm* — Rankin, Hill & Clark LLP

(57) ABSTRACT

Method for the determination of *Trichinella* infections in an animal or a human, comprising the incubation with *Trichinella* antigens of a tissue sample taken from the animal or the human, the processing of the tissue sample, the addition of anti-antibodies to the tissue sample, and the verification of whether binding of the anti-antibodies to any antigen/antibody complexes present in the tissue sample has taken place, where the anti-antibodies added are anti-IgG antibodies and simultaneously anti-IgM antibodies.

6 Claims, 2 Drawing Sheets

Figure 1:
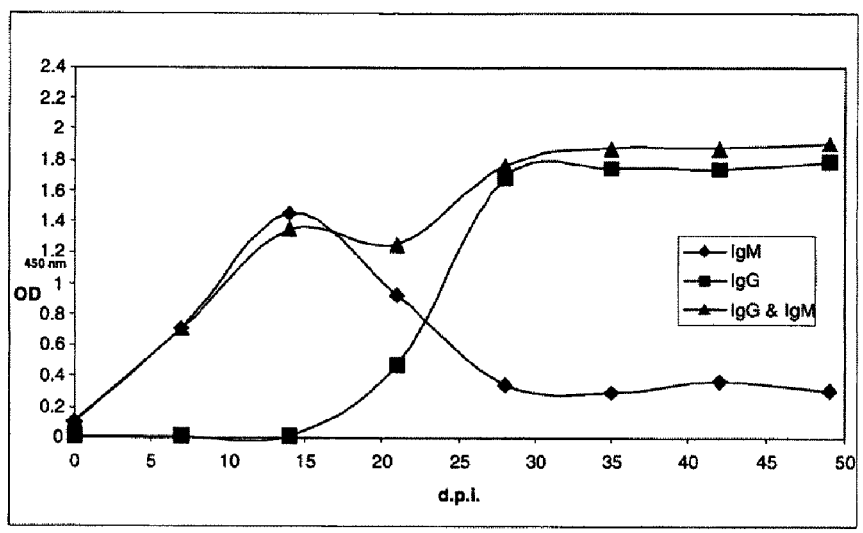

METHOD FOR THE DETERMINATION OF *TRICHINELLA* INFECTIONS AND DIAGNOSTIC COMPOSITION FOR SUCH METHODS

The invention relates to a method for determining *Trichinella* infections in an animal or a human, and to a diagnostic composition for use in such method.

*Trichinella* spp. comprises a group of cosmopolitan nematodes. The species which predominate in Europe are *Trichinella spiralis*, *Trichinella britovi*, *Trichinella pseudospiralis* and *Trichinella nativa*. *Trichinella* infections may occur in different species including humans, pigs, rats, bears, horses and birds, to mention only a few examples.

*Trichinella* species are parasitic nematodes which undergo a defined life cycle. The larvae are taken up by consuming raw or insufficiently cooked meat. After consumption, they are released by the gastric juices, from where they reach the intestinal tract. This is where they grow into adult nematodes. After mating, the females produce up to 1500 new larvae, which, via the lymph and the blood circulation, penetrate the striated muscle tissue, in particular the diaphragm, the tongue, the eye and the jaw muscles. The larvae grow and develop larval complexes which calcify with the course of time.

*Trichinella* infections pose a massive problem in animal production. It must be ruled out with certainty that humans will not contract trichinellosis after consuming raw or insufficiently cooked meat from diseased animals. Human trichinellosis is a serious disease which causes considerable illness and is lethal in extreme cases.

To ensure food safety, therefore, for example all porcine carcasses must be tested as part of a post-mortem inspection. As a rule, the carcasses are processed immediately after slaughtering. The problem with current tests is that cutting, on the cutting premises which follow the slaughterhouse, will have been finished to a certain degree before the results of the *Trichinella* tests are available. This poses a considerable logistic problem. In case of doubt, the cut pig portions will, if results are positive, have to be picked out again from the processing cycle and destroyed.

Methods which are approved currently are those in which *Trichinella* is detected directly. An earlier method which, in Europe, is approved during a transitional period only, is what is known as trichinoscopy, where tissue is pressed between two glass sheets and then viewed under the microscope. This method is fairly insensitive and, moreover, requires a great deal of labor and time. Furthermore, *Trichinella* species which do not encapsulate such as, for example, *Trichinella pseudospiralis*, can be detected with great difficulty only, or not at all.

A further approved method is what is known as the digestion test, which is more sensitive than the above-described direct detection. In this test, the muscle tissue which surrounds the larvae is digested artificially using proteases and hydrochloric acid and the larvae remain after a variety of sedimentation steps. Thereafter, the number of larvae can be determined under the microscope. The detection limit is 3 to 5 larvae per gram of tissue.

Methods which are much more rapid and considerably more sensitive are generic serological methods, in which antibodies against *Trichinella* spp. are detected, in most cases indirectly. Such serological methods can be carried out for example on blood serum or meat juice. The customary methods have a detection limit of 0.01 larva per gram of muscle tissue.

In generic serological methods, for example serum samples from the organism to be tested are treated with *Trichinella* antigens, for example the excretory/secretory (E/S) antigen. Any antibodies which may be present in the serum as the result of a *Trichinella* infection bind to the antigen. The bound antibodies, in turn, are detected for example using labeled anti-swine IgG antibodies. Customary serological methods work for example with immobilized antigens and detect any bound IgG antibodies. Specific further antigens which are suitable for serological methods are disclosed for example in WO 2007/090960.

Although generic serological methods are highly sensitive, they are currently not approved for meat inspection or in food safety programs. While serological methods are more rapid and more sensitive that the direct tests such as, for example, artificial digestion, the current EU regulations will nevertheless not allow the individual testing of carcasses by serological methods because the known serological methods may give false-negative results, in particular during the early phase of the infection. A similar attitude is held by the international Trichinellosis commission (ICT). Again, the criticism is that the diagnostic window for serological methods is insufficient and that animals which may be positive are not picked up by the available methods because the signal during the early infection phase is not strong enough. Since, however, the larvae even during this phase may already be in the muscle, and can therefore be infectious, even animals in the early infection phase must be identified reliably.

It is the object of the present invention to provide a reliable serological method for diagnosing *Trichinella* infections, by means of which method not only early infections, but also advanced *Trichinella* infections, can be detected reliably. A further object is to provide a diagnostic composition which is suitable for such a method.

The object is achieved by a method and a diagnostic composition as disclosed herein. Advantageous embodiments are specified below.

The method according to the invention works essentially as specified hereinabove. A sample of the human or animal to be tested, for example serum or meat juice, is incubated together with, preferably immobilized, antigens. Any antibodies which are present in the sample bind to the antigens. The antibody/antigen complexes are then detected by means of labeled antibodies. This may be performed in particular by an ELISA method. However, other methods which employ other labels, for example labels which can be detected visually, are also feasible.

As has already been mentioned above, traditional *Trichinella* tests detect the antibody/antigen complexes with antibodies against IgG antibodies, since these are the persistent antibodies usually produced increasingly over the course of the infection.

According to the invention, there is now provided that a simultaneous examination be carried out to determine if IgM antibodies have been formed. This can be effected in a simple manner by adding antibodies against IgM antibodies.

Accordingly, there is provided in accordance with the invention that the sample be examined for the presence of IgM and IgG antibodies in combination. During the early phase of the infection, it is predominantly IgM antibodies which are formed, while the IgG antibody content only starts from day 15 post-infection. At this point in time, approximately, the IgM antibody content starts to drop again.

The drop in the IgM antibody content which can be observed relatively soon post-infection is also an important reason why for example ELISA methods, in which IgM antibodies are determined, should be considered not suitable for the diagnosis of *Trichinella* infections. By way of representation, reference is made to a PhD thesis titled "The usefulness of ELISA test for early serological detection of *Trichinella* spp. infection in pigs" which had been carried out at the "Department for Parasitology" in Warsaw, Poland, and which was presented in 2006 in a viva. The PhD thesis compares methods in which IgG antibodies on the one hand and IgM antibodies on the other hand are detected. In this paper it was found that ELISA methods, in which IgG antibodies are detected, are suitable in principle for detecting *Trichinella* infections. IgM antibodies, in contrast, were considered to be unsuitable markers of the humoral response of infected animals. An essential reason was that, at least according to the opinion voiced in the paper, *Trichinella spiralis* in particular cannot be detected. A further reason is of course that the IgM concentration will drop again at a relatively early point in time, and that the diagnostic window will, therefore, only detect early infections.

In their own studies, which will be illustrated further hereinbelow with reference to FIGS. 1 and 2, the applicants have found that antibodies of the IgM class are also produced in *Trichinella* spiralis infections and can be detected by, for example, ELISA. Contrary to the opinion voiced, IgM antibodies therefore appear to be markers which are suitable in principle, after all, for determining early *Trichinella* infections.

From the moment of *Trichinella* infection, an immune response is present in the organism, which response can be detected a few days later using the method according to the invention. As demonstrated in FIG. 1 or 2, it is first the IgM antibodies which are detected, later during the course of the infection IgM and IgG antibodies and then increasingly only IgG antibodies.

The method according to the invention therefore identifies an infection considerably earlier than the previously known methods and therefore reduces the diagnostic window (see also FIG. 3, which is discussed hereinbelow).

The test designed by the applicants, in which for the first time both antibody responses are detected simultaneously, surprisingly allows to overcome the essential disadvantages of known serological methods.

Within the scope of the invention, it is possible generally to detect, in a sample, the presence of an antibody response to a *Trichinella* infection, without assigning the antibodies to a class. If additionally it is also desired to know whether the infection stage is an early or a later one, then it is also possible to provide the anti-antibodies used in the method according to the invention with different labels, depending on whether they are intended to detect IgG or IgM antibodies.

As mentioned hereinabove, *Trichinella* antigens are added to a sample both in traditional and in the inventive serological method. The antigens may in particular take the form of the E/S antigen. However, further immunogenically-acting polypeptides, either individually or in combination, are also feasible, for example those which are described in the international patent application PCT/EP2007/005774 or in WO 2007/090960.

Naturally, it is also possible to employ a plurality of different antigens, in particular antigens which are produced at different infection stages. In this manner, better binding opportunities may under certain circumstances be provided for any antibodies which may be present, which likewise leads to an improved statement.

To simplify the detection of any antigen/antibody complexes formed, it is preferably provided that the antigens be employed in immobilized form. For example, it is feasible that the walls of microtiter plates be coated with the antigens.

A further possibility is to bind the antigens to beads. In principle, suitable immobilization methods are all those with which the antibodies and any antibodies bound thereto can be separated in a simple manner from the remainder of the sample.

Furthermore, it is provided in accordance with the invention that the anti-antibodies have a label which can be detected with customary methods. This may take the form for example of a label which is suitable for an ELISA detection. However, other labels, for example visually detectable labels such as, for example, fluorescent labels, are also feasible.

The tissue samples tested may in particular take the form of blood, serum, plasma, meat juice.

Besides a method, the invention also relates to a diagnostic composition which can be employed in the method according to the invention.

According to the invention, such a composition comprises a suitable, in particular immobilized, *Trichinella* antigen and anti-IgG and anti-IgM antibodies which are provided with a label which permits detection. Preferably, the *Trichinella* antigens and the anti-antibodies are manufactured separately so that a contact between the antigens and the tissue sample can first be established and then the anti-antibody can be added after a suitable incubation period.

The *Trichinella* antigen is preferably provided in immobilized form. Feasible forms are, for example, coupling to beads or coating of the walls of microtiter wells with the antigen, to mention only a few.

Essentially, the purpose of the immobilization of the antibody is to allow any antigen/antibody complexes to be separated from the sample in a simpler manner. This separation simplifies the specific detection of the complexes.

Besides heterogeneous assays, homogeneous assays, i.e. methods in which the antigen is not present in immobilized form, are, naturally also feasible. A preferred method might be for example a fluorescence polarization assay. A person skilled in the art is familiar with carrying out such a method. This will therefore not be discussed in greater detail.

As has already been mentioned about the method, the composition comprises as antigen preferably what is known as the E/S antigen from *Trichinella* or immunogenic segments of this antigen. Naturally, the use of other polypeptides from *Trichinella* with antigenic activity is also feasible. In principle, all peptides or polypeptides which have a series of amino acids which form a continuous or discontinuous epitope recognized by sera obtained from *Trichinella*-infected pigs may be employed.

Naturally, the combination of a plurality of different antigens in the composition according to the invention is also feasible. The antibodies may be present as a mixture. However, it is also feasible to provide them for example coupled with each other in the form of a fusion protein.

Finally, the labels on the anti-antibodies can be designed such that they make possible a simple visual detection. However, it is preferred to employ ELISA methods. Naturally, the anti-antibodies can therefore also be coupled with suitable enzymes which make possible the desired ELISA detection.

The embodiments described in conjunction with the composition can, naturally, also be realized analogously within the scope of the method according to the invention, in as far as they have not been mentioned already in that context.

Figure 2:
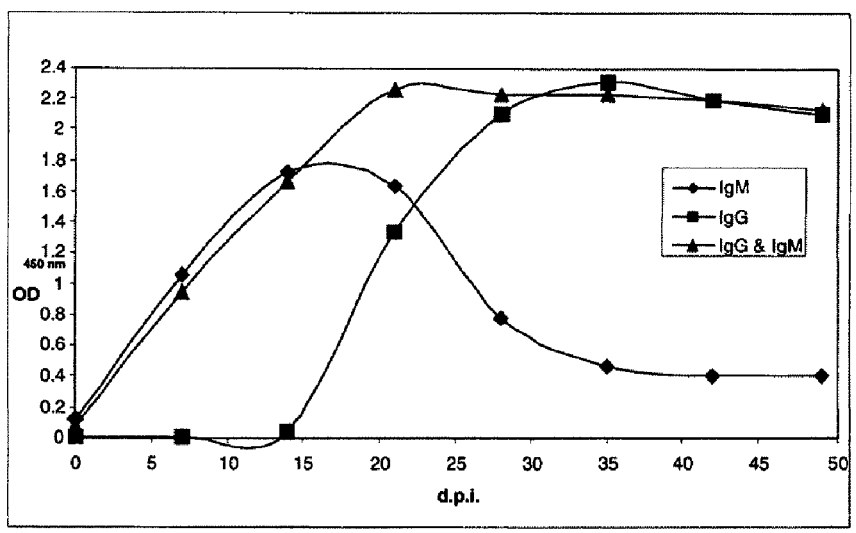

In what follows, the invention shall be illustrated in detail with reference to a plurality of figures in which FIG. 1 and FIG. 2 show a schematic representation of the results of ELISA methods when determining the immune response of pigs which have artificially been orally infected with 20 000 *T. spiralis* larvae and FIG. 3 (A)-(C) shows a schematic representation of the diagnostic windows covered by different methods when identifying *Trichinella* infections.

FIGS. 1 and 2 show in each case the results of 3 ELISA methods. What is shown is in each case the course of the IgG (■), the IgM (♦) and the combined (▲) IgG and IgM response to *Trichinella* infection at different points in time.

The pigs were artificially orally infected with 20 000 *T. spiralis* larvae, and serum samples of the infected pigs were tested at different points in time. FIG. 1 and FIG. 2 show the results of tests which were carried out under identical conditions on samples obtained from different herds of pigs.

Samples were taken on days 0, 7, 14, 21, 28, 35, 42 and 49 after the infection (d.p.i.=days post-infection). It emerged that the combined detection of the IgM and IgG response could be detected as early as on day 7 post-infection and is then retained over the entire life of the animal.

Also shown are the IgM reactions, which can be measured relatively soon after the infection, and the IgG reaction, which is detectable approximately from day 15 and then relatively constantly throughout the remaining life of the animal.

The two FIGS. 1 and 2 show similar courses of the above-mentioned reactions.

Figure 3:
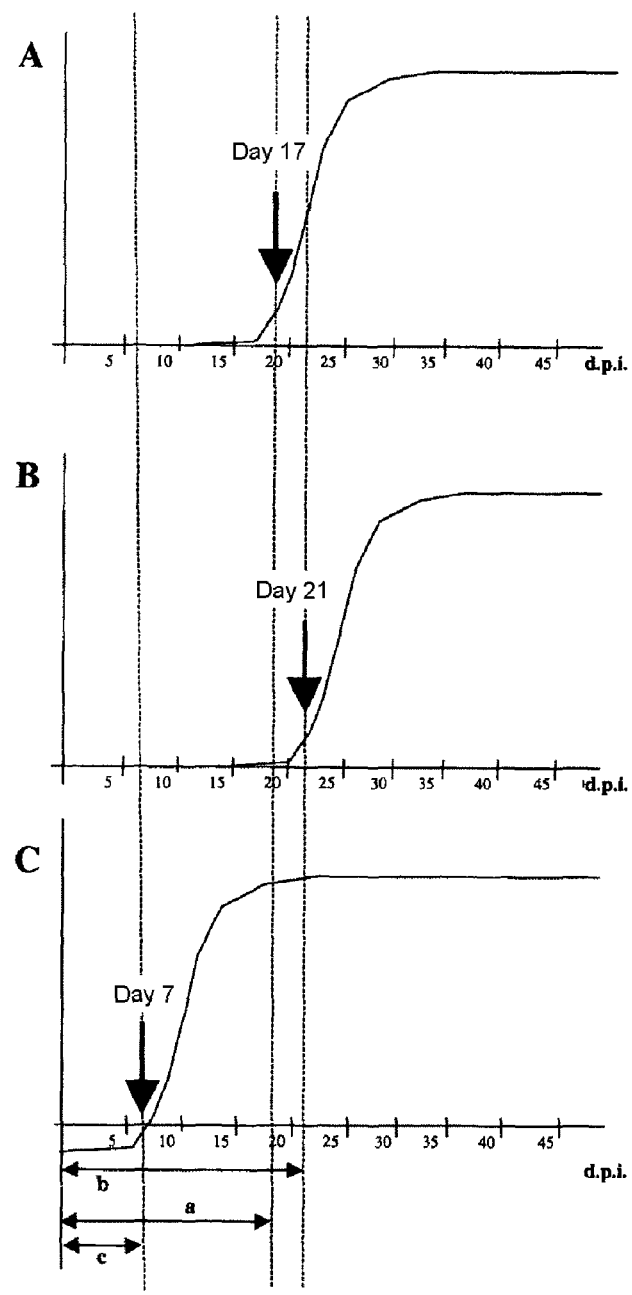

FIG. 3 (A)-(C) shows a diagram of the diagnostic windows covered by different methods [(A)=digestion test; (B)=conventional E/S ELISA and (C)=ELISA according to the invention] in the identification of *Trichinella* infections.

FIG. 3 (A) shows that the earliest point in time at which a *Trichinella* infection can be detected in the artificial digestion test is day 17 post-infection.

FIG. 3 (B) shows the conditions in the identification of *Trichinella* infections in pigs using a conventional E/S ELISA method. Here, it emerges that a detection of an immune response with a conventional serological method is possible on day 21 post-infection at the earliest. At this point in time, larvae may already be infectious.

FIG. 3 (C), however, shows the conditions for the inventive method in the identification of *Trichinella*-infected pigs. The earliest point in time at which an antibody response can be detected in samples from *Trichinella*-infected pigs is day 7 post-infection. This is markedly earlier than in the two methods shown under (A) and (B). On day 7, the larvae are not infectious yet. It can therefore be concluded that the method according to the invention makes possible a sufficiently reliable determination of *Trichinella* infections.

The comparison of the different detection methods in (A), (B) and (C) is shown by dotted lines. b denotes the diagnostic window for conventionally used E/S ELISA (B), a the diagnostic window for the artificial digestion test (A), while c shows the diagnostic window for the ELISA method (C) according to the invention. Again, this representation makes it clear that the method according to the invention allows the detection of infected pigs at a significantly earlier point in time. The diagnostic window thereby becomes markedly narrower, and a detection of a *Trichinella* infection is possible even earlier than with the artificial digestion test and makes such a diagnostic method suitable for individual meat testing in slaughterhouses.

We claim:

1. A method for the determination of *Trichinella* infections in an animal or a human, comprising:
    incubating a tissue sample taken from the animal or the human together with a *Trichinella* antigen that is capable of forming a *Trichinella* antibody/antigen complex with *Trichinella* antibodies that may be present in the tissue sample;
    adding both anti-IgG antibodies and anti-IgM antibodies to the incubated tissue sample; and
    testing whether a binding of both of the anti-IgG antibodies and the anti-IgM antibodies has taken place with a *Trichinella* antibody/antigen complex which may be present in the tissue sample.

2. The method as claimed in claim 1, wherein the the *Trichinella* antigen that is capable of forming *Trichinella* antibody/antigen complex with *Trichinella* antibodies is *Trichinella* E/S antigen.

3. The method as claimed in claim 1, wherein the *Trichinella* antigen employed is present in immobilized form.

4. The method as claimed in claim 1, wherein labeled anti-IgG antibodies and anti-IgM antibodies are employed.

5. The method as claimed in claim 1, wherein the anti-IgG antibodies are provided with a different label than anti-IgM antibodies.

6. The method as claimed in claim 1, wherein the tissue sample is one or more selected from the group consisting of serum, plasma and meat juice.

* * * * *